United States Patent [19]

Chaux

[11] Patent Number: 4,852,552
[45] Date of Patent: Aug. 1, 1989

[54] STERNAL RETRACTOR
[75] Inventor: Aurelio Chaux, Los Angeles, Calif.
[73] Assignee: Pilling Co., Fort Washington, Pa.
[21] Appl. No.: 92,640
[22] Filed: Sep. 3, 1987
[51] Int. Cl.[4] .................................................. A61B 17/02
[52] U.S. Cl. ......................................................... 128/20
[58] Field of Search ...................................... 128/17–20, 128/345

[56] References Cited

U.S. PATENT DOCUMENTS

| | | | |
|---|---|---|---|
| 3,572,326 | 3/1971 | Jensen | 128/20 |
| 4,355,631 | 10/1982 | LeVahn | 128/20 |
| 4,627,421 | 12/1986 | Symbas et al. | 128/20 |
| 4,702,230 | 10/1987 | Pelta | 128/20 |
| 4,726,356 | 2/1988 | Santilli et al. | 128/20 |

FOREIGN PATENT DOCUMENTS

| | | | |
|---|---|---|---|
| 1019217 | 1/1953 | France | 128/20 |
| 156267 | 3/1964 | U.S.S.R. | 128/20 |

OTHER PUBLICATIONS

"Internal Mammary Retractor", R. A. Beg, H. Naraghipour & E. B. Kay & P. Rullo, Ann. Thoracic Surg. 39:286, 1985.
"A Modified Sternal Retractor", N. Ancalmo and J. L. Ochsner, Ann. Thoracic Surg. 21: 174, 1976.
"A Modified Sternal Retractor for Exposure of the Internal Mammary Artery", P. P. McKeown, J. Crew, E. S. Hanna, & R. Jones, Ann Thoracic Surgery 32:619, 1981.
Advertisement of Delacroix-Chevalier entitled "Une Revolution Francaise", undated.
"A New Concept in Sternal Retraction: Applications for Internal Mammary Artery Dissection and Valve Replacement Surgery", Chaux, A., Blanche, C. Ann. Tthoracic Surg. 42:473-474, 1986.

Primary Examiner—Edward M. Coven
Assistant Examiner—Mark J. Graham
Attorney, Agent, or Firm—Howson & Howson

[57] ABSTRACT

A sternal retractor for use in internal mammary artery dissection comprises a rack bar having fixed and movable spreader arms, the blade-carrying parts of which are rotatable to, and lockable in, several discrete positions. The blades are carried by slides on the spreader arms, and are pivotable about two mutually perpendicular axes which are also perpendicular to the arms, but restrained against rotation about axes extending lengthwise of the arms. One of the slides disclosed is provided with an undercut slot to receive a post for mounting auxiliary retractors. This makes the retractor especially useful for various operation in addition to internal mammary artery dissection.

4 Claims, 2 Drawing Sheets

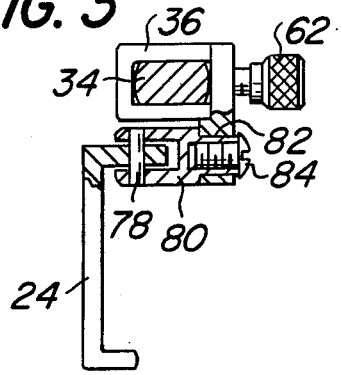
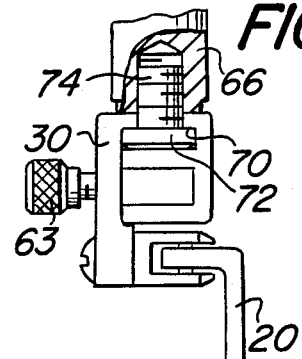
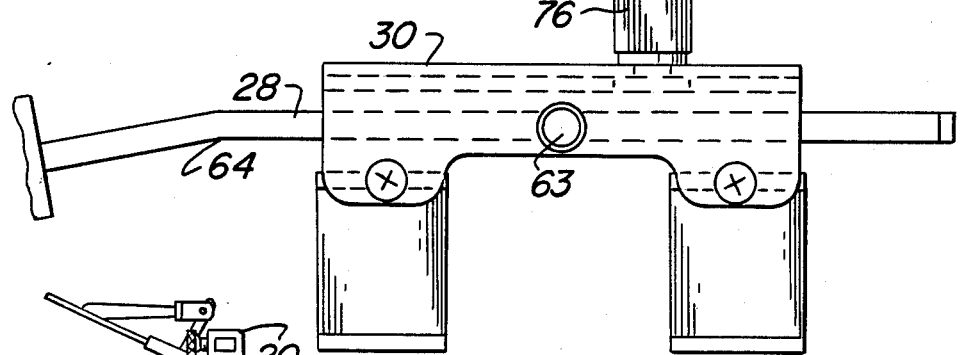
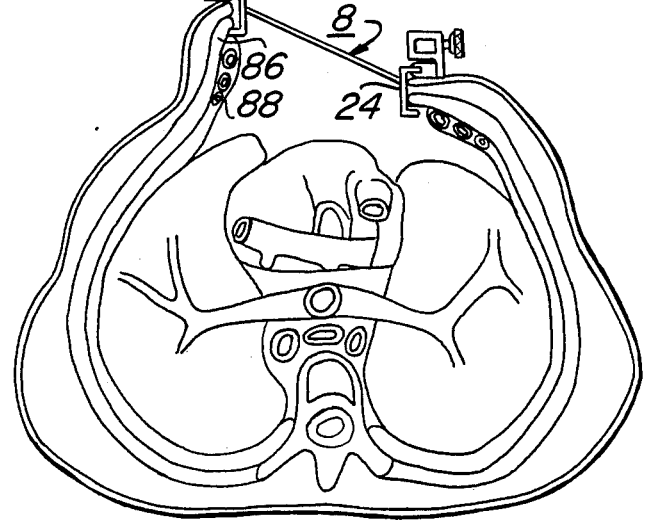

STERNAL RETRACTOR

BRIEF SUMMARY OF THE INVENTION

This invention relates to surgical retractors, and particularly to a novel sternal retractor useful in chest surgery in general, and having particular utility in internal mammary artery dissection.

In coronary bypass surgery, a blood vessel, usually taken from another part of the patient's body, is grafted onto the heart as a bypass for a diseased coronary artery. In some cases, the saphenous vein is taken from the patient's leg for this purpose. In others, the internal mammary artery is preferred because of its high velocity flow, and its long term patency and immunity to failure.

To obtain access to an internal mammary artery it is necessary to cut through and retract the sternum, and to raise one side of the sternum to expose the interior of the chest wall, on which the artery is located. Several different kinds of retractors have been used in the past for this purpose.

One retractor, described in U.S. Pat. No. 4,355,631, consists of a framework attached to the operating table with individual retractor blades having shafts clamped to the framework. A similar retractor is described in U.S. Pat. No. 3,572,326.

Another retractor for internal mammary dissection is described in Beg. R.A., Naraghipour, H., Kay, E. B., and Rullo, P: Internal Mammary Retractor, Ann. Thoracic Surg. 39:286, 1985. It consists of an upstanding post attachable to the operating table, a ratchet-equipped winch mechanism having a flexible cable attached to one corner of a triangular force distributor. Two retractor elements, each consisting of a rake-type blade and a shaft, are articulably joined to the edge of the triangle opposite the corner to which the cable is attached. This retractor exerts an upward and outward force on the chest wall to provide exposure of the internal mammary artery.

Another retractor useful for internal mammary dissection is known as the Ochsner-Favoloro self-retaining retractor. It is described in Ancalmo, N., Ochsner, J. L.: A Modified Sternal Retractor, Ann. Thoracic Surg., 21: 174, 1976. This retractor comprises a pair of posts adapted to attach to an operating table, with a cross-member extending between them. Blocks are adjustably clamped onto the cross-member, and retractor blades with threaded shafts extend through holes in the blocks and are adjustably tensioned by adjusting knobs threaded onto the shafts above the blocks.

Hand-held retractors are sometimes used for internal mammary dissection. A hand-held retractor, specially designed for this purpose is described in McKeown et al.: A Modified Sternal Retractor For Exposure of the Internal Mammary Artery, Ann. Thoracic Surg., 32:619, 1981. It comprises a blade having an S-shaped handle with a cross-member for engaging the outer chest wall in order to provide leverage for lifting the sternum.

Standard sternum spreading retractors have also been used in internal mammary dissection. A sternum spreading retractor has a pair of parallel arms with retractor blades. One arm is fixed to a toothed rack bar, and the other is movable along the bar by a crank-operated pinion. In most, if not all, cases, the sternum spreading retractor is constructed so that if the rack bar is positioned toward the patient's feet, the fixed arm is on the patient's right side and the movable arm is on the patient's left, To lift the left side of the sternum, a folded towel is placed under the portion of the toothed bar extending beyond the movable arm of the retractor on the left side of the patient. A typical sternum spreading retractor used for internal mammary dissection is known as a Morse Sternal Spreader. Each arm has two blades pivoted thereon for swivelling about generally vertical axes. The arms are usually bent slightly to conform to the sternum, so that one blade is on a portion of the arm which is slightly oblique in relation to the portion of the arm having the other blade.

The retractors used heretofore in internal mammary dissection are subject to a number of problems which may be summarized as follows.

The retractor assemblies which attach to the operating table are generally complex, and in some cases constitute an obstruction interfering with the work or vision of the surgeon's assistants. Another problem is that the bars and other suspension mechanisms which are attached to the operating table are outside the sterile field, and can cause problems in maintaining sterile conditions.

Hand-held retractors are, of course, tiring to use and require one or more additional assistants in surgery.

Standard sternal spreading retractors avoid the foregoing problems, but require the use of a folded towel under the toothed arm, or some alternative auxiliary means, to lift one side of the sternum to gain access to the internal mammary artery. When the side of the sternum is lifted, the blades tend not to conform as well to the sternal edges. Even in the case of a Morse Sternal Spreader, which has swivelling blades, good conformity of the blades to the sternal edges is not achieved, and undesired fractures or tissue damage can result if excessive forces are applied by the retractor. Another problem with conventional sternal retractors is that in the case of a large patient with a long internal mammary artery, the toothed bar tends to get in the way of the surgeon performing the dissection. If the same retractor is used to remove the right mammary artery, the toothed bar, which must be positioned toward the patient's head in order to be lifted in the proper direction by a folded towel on the right side of the patient's chest, may be interfered with by the patient's chin.

The principal object of the invention is to overcome the above problems by providing a retractor for internal mammary artery dissection which is structurally simple, which does not obstruct the surgeon or the surgeon's assistants, which is situated in use entirely within the sterile field, which does not require an assistant merely to hold the retractor and which does not require an auxiliary device to lift one-half of the sternum. Another object of the invention is to avoid injury to the patient resulting from excessive forces applied by the retractor. Still another object of the invention is to provide a retractor which is adjustable so that it can be used for dissection of both the right and left mammary arteries, and so that it can be used on patients of widely different sizes. It is also an object of the invention to provide a retractor with maximum adjustability to facilitate internal mammary artery dissection. Still another object of the invention is to achieve a firm grip on the edges of the sternum and at the same time to cause a gentle separation of the sternal halves to avoid fractures or dislocations of the sternum or costochondral junctions. Other objects will be apparent from the following detailed description and the drawings.

BRIEF DESCRIPTION OF THE DRAWINGS

FIG. 3 is a partially cut-away elevational view taken through plane 3—3 of FIG. 1;

FIG. 4 is a partially cut-away elevational view taken through plane 4—4 of FIG. 1;

FIG. 5 is a fragmentary side elevation of the retractor, as viewed from the left-hand side of FIG. 1; and FIG. 6 is a vertical section through a patient showing the retractor in use.

DETAILED DESCRIPTION

Figure 1:
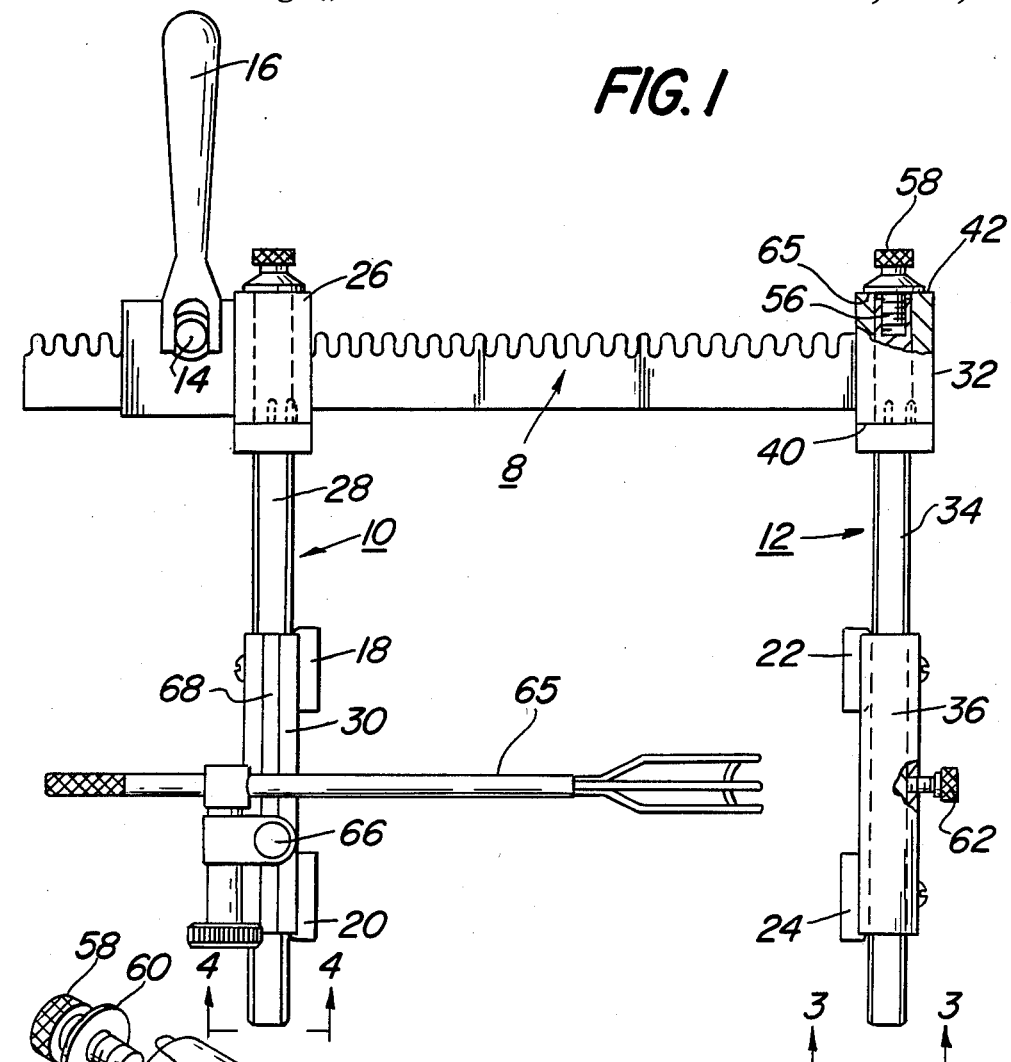
FIG. 1 is a top plan view of a sternal retractor in accordance with the invention.

The retractor of the invention comprises a rack bar 8 and a pair of spreader arms 10 and 12. The position of arm 12 is fixed at one end of rack bar 8, while arm 10 is movable along the rack bar by a pinion (not shown) on shaft 14, which is manually rotatable through crank 16. Arm 10 carries retractor blades 18 and 20, and arm 12 carries retractor blades 22 and 24.

Arm 10 comprises a first part 26, which is a body movable along the rack, a second part 28 which is preferably in the form of an elongated arm having a chamfered rectangular cross-section, and a slide 30. Elongated second part 28 is rotatable relative to first part 26 about an axis along its direction of elongation, but the two parts are normally locked against such rotation. Slide 30 is movable along elongated part 28, but is likewise normally locked against such movement. Arm 12 consists of a similar first part 32, an elongated second part 34 and a slide 36.

Figure 2:
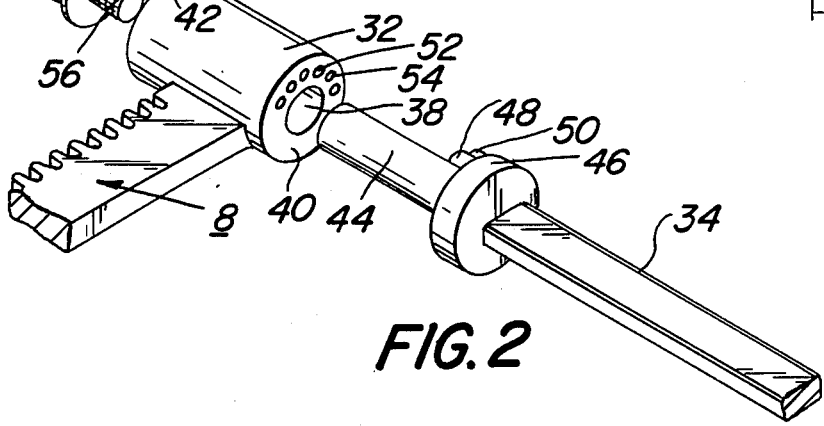
FIG. 2 is a fragmentary exploded view showing how the rotatable part of a spreader bar of the retractor is adjustably secured to the non-rotatable part.

As shown in FIG. 2, part 32, which is preferably fixed at one end of rack 8, has a circular cylindrical through passage 38 extending from a face 40 at one end to a face 42 at its opposite end. A cylindrical projection 44 of arm 34 is designed to fit into passage 38, conforming closely to the interior wall thereof. Cylinder 44 extends almost to the opening at face 42, as shown in FIG. 1. A collar 46 on part 34 is engageable with face 40, and has a pair of pins 48 and 50 which are adapted to enter any adjacent pair of holes in a series of holes, including holes 52 and 54, arranged about the opening of passage 38 equidistant from the axis thereof. Engagement of the pins in the holes in face 40 locks part 34 against rotation relative to part 32. Screw 56 is threaded into a threaded opening at the end of cylinder 44 by tightening head 58 until shoulder 60 of the screw engages face 42, as shown in FIG. 1. In this manner, part 34 is releasably locked to part 32 in one of several selectable discrete rotational relationships. Part 28 of the movable spreader arm 10 is similarly adjustably locked to part 26.

As shown in FIGS. 1 and 3, slide 36 is clamped to elongated part 34 of arm 12 by set screw 62. Slide 30 is likewise clamped to part 28 by set screw 63, as illustrated in FIGS. 4 and 5. Parts 28 and 34 of the spreader arms are substantially parallel to each other. So that the retractor can lie as near as possible to the patient's chest during surgery, part 28 is preferably bent slightly at 64, as shown in FIG. 5, and part 34 is similarly bent. At the bend is only a slight one, parts 28 and 34 can be considered as substantially straight and as extending along their axes of rotation. Slides 30 and 36 are adjustable along the straight major portions of the elongated elements by releasing set screws 62 and 63.

Slide 30 is adapted to receive an auxiliary retractor 65, which can be used in mitral valve surgery. Referring to FIGS. 1, 4 and 5, retractor 65 is clamped to a post 66, which engages the upper face of slide 30. This face has a slot 68 extending at least to one end of the slide and preferably to both ends. The slot is undercut at 70 to receive rectangular head 72 of a screw, the shank 74 of which extends upwardly through the slot and into a threaded opening in the bottom of post 66. Post 66 is tightened against the upper face of slide 30 by rotation of its knurled collar 76. Rectangular head 72 is not rotatable in the undercut portion of the slot, and consequently it is possible to secure post 66 in position merely by rotation of the post itself.

Each of blades 18, 20, 22 and 24 has two degrees of freedom for pivoting movement relative to the spreader arm on which it is mounted. For example, as shown in FIG. 3, blade 24 is supported on pivot pin 78, which extends substantially through bifurcated element 80, perpendicular to the direction of the axis of rotation of part 34. The bifurcated element has an extension 82, which extends substantially perpendicular to pin 78, through a hole in a flange extending lengthwise along the bottom of slide 36. Extension 82 terminates at a point slightly beyond the outer face of the flange. A screw 84 is threaded into the end of extension 82, and its head is tightened against the end of the extension, but not against the face of the flange. This way, element 80 can rotate about the axis of extension 82. Consequently, blade 84 is pivotable about the axis of pin 78 and about the axis of extension 82, these two axes being substantially perpendicular to each other and to the axis of rotation of part 34. Blade 24, however, is prevented by pin 78 and bifurcated element 80 from rotation about the axis of rotation of part 34. Each of the other blades is similarly mounted for pivoting movement about two substantially perpendicular axes, and is prevented from rotation about a spreader arm rotation axis to which the other two axes are both substantially perpendicular. The blades are pivotable at least to a limited degree to allow them to conform automatically to the sternal edges. The blades, however, cannot rotate about axes extending lengthwise of the spreader arms, the attitude of the blades on these axes being determined by the relationship of the second parts of the spreader arms to the cylindrical bodies attached to the rack bar.

As shown in FIG. 6, the fixed spreader arm of the retractor is adjusted counterclockwise, and positioned against the sternal edge on the right side of the patient. The movable spreader arm is likewise adjusted counterclockwise and positioned against the sternal edge on the left side of the patient. When the retractor is in place, the surgeon tilts the retractor so that the movable arm is slightly raised. Thereafter, when the elements of the retractor are moved apart by the operation of the rack and pinion, the counterclockwise adjustment of the spreader arms causes the left side 86 of the sternum to be automatically lifted to provide access to the left internal thoracic vascular pedicle 88 for dissection. The ability to adjust blade attitude also has the advantage that it allows the blades to be positioned to grasp the sternal edges firmly to avoid possible slippage and disengagement, which could occur with a conventional sternal spreader. An important advantage of allowing the blades to pivot in two directions is that it provides improved compensation for misalignments between the blades and the sternal edges which result when the retractor arms are twisted.

If the retractor were reversed, so that the rack bar is positioned toward the patient's head, but with the attitudes of the blades unchanged, the right side of the patient's chest would be lifted when the retractor arms are spread apart.

The several discrete positions for adjustment of the blade attitudes allow the surgeon to adjust the retractor as desired to take into account differences between patients. Furthermore, different degrees of tilting of the blades may be needed, depending on whether the instrument is being used for left or right internal mammary dissection. The engagement of pins in holes to secure the blades at the desired attitude relative to the rack bar insures against accidental slippage, while still providing a high degree of flexibility for the surgeon.

Additional adjustability is provided by longitudinal adjustment of the slides. Their positions relative to the rack bar can be adjusted by the surgeon to adapt the retractor the length of the patient's sternum. The slides are independently adjustable relative to each other, and such adjustment may be desirable in certain cases.

To dissect the right internal mammary artery, preferably the blade-carrying slides are moved toward the rack bar and locked in position. The rack bar is positioned toward the patient's head. The arms are both rotated counterclockwise about thirty degrees, and the blades are positioned at the level of the distal portion of the sternum and opened progressively by operation of the rack. When the rack is operated, the right side of the sternum is raised.

To dissect the left internal mammary artery, the retractor is preferably adjusted so that the blades are near the ends of the retractor arms remote from the rack bar. The arms are rotated counterclockwise about thirty degrees, or more if necessary, and the rack bar is located toward the patient's abdomen, with the blades placed either at the mid third or slightly toward the lower third of the sternum. When the rack is operated, the left side of the sternum is raised.

In bilateral internal mammary artery dissection, the right artery is preferably dissected first, which the rack bar toward the patient's head. After dissection of the right artery the retractor is removed, readjusted and reversed so that the rack bar is toward the patient's abdomen. The surgeon then proceeds to expose the left artery.

Following internal mammary dissection, the arms of the retractor can be rotated to a neutral position, and the retractor can then be used as a standard sternal retractor.

The retractor, while specially adapted for internal mammary artery dissection, can be used wherever sternal retraction is required in surgery. If it is equipped with one or more slotted slides corresponding to slide 30, auxiliary retractors can be conveniently supported on the slides with a minimum of intrusion into the space available for the surgeon.

Numerous modifications can be made to the retractor specifically described. For example, instead of using pins and holes to accomplish locking of the movable part of the spreader arms to the fixed parts, as depicted in FIG. 2, the engaging faces of body 32 and collar 45 can be provided with interengaging teeth, which will hold the parts of the spreader arm in fixed relationship to each other when screw 56 is tightened. Alternative forms of rack bars can be used, such as rack bars with ratchet teeth. If desired, both spreader arms can be made movable along the rack bar. Numerous other modifications can be made to the apparatus herein described without departing from the scope of the invention as defined in the following claims.

I claim:

1. A sternal retractor for use in internal mammary artery dissection comprising:

a rack bar;

a pair of spreader arms connected to the rack bar, said spreader arms being sufficiently straight to conform to a sternal incision and extending substantially perpendicular to the rack bar and substantially parallel to each other, one of the spreader arms being movable along the rack bar whereby the spacing between the arms can be adjusted;

means connected to the rack bar and to the spreader arm movable thereon for applying a force causing the spreader arms to separate from each other while being maintained in substantially parallel relationship to each other;

means for engaging and spreading split sternal halves comprising sternum-engaging retractor blade means attached to each of said spreader arms;

at least one of said spreader arms comprising a first part connected to the rack bar and a second part extending beyond the first part in a direction away from the rack bar, said second part carrying the sternum engaging retractor blade means on said one of said spreader arms, means joining and locking said first and second parts against relative rotation about an axis of relative rotation substantially parallel to the arm, said joining and locking means being disengagable to allow adjustment of the rotational relationship of the first and second parts about said axis, and being capable of positively locking said first and second parts together only in a predetermined limited number of discrete rotational relationships; and pivot means for connecting sternum-engaging retractor blade means to said one of said spreader arms, the pivot means permitting rotation of each of the sternum-engaging blade means on said one of said spreader arms about first and second axes, said first and second axes being substantially perpendicular to each other and being both substantially perpendicular to the axis of relative rotation of the first and second parts of said one of said spreader arms but preventing rotation of said sternum-engaging retractor blade means about said axis of relative rotation.

2. A sternal retractor for use in internal mammary artery dissection comprising:

a rack bar;

a pair of spreader arms connected to the rack bar and extending substantially perpendicular to the rack bar and substantially parallel to each other, one of the spreader arms being movable along the rack bar whereby the spacing between the arms can be adjusted;

means connected to the rack bar and to the spreader arm movable thereon for applying a force causing the spreader arms to separate from each other while being maintained in substantially parallel relationship to each other; and means for engaging and spreading split sternal halves comprising sternum-engaging retractor blade means attached to each of said spreader arms;

at least one of said spreader arms comprising a first part connected to the rack bar and a second part carrying the sternum-engaging retractor blade means on said one of said spreader arms, means joining and locking said first and second parts against relative rotation about an axis of relative rotation substantially parallel to the arm, said joining and locking means being disengagable to allow adjustment of the rotational relationship of the first and second parts about said axis;

in which said first part connected to the rack bar comprises a body having first and second faces respectively on opposite sides thereof, and a cylindrical passage extending therethrough from the first face to the second face, the axis of the cylindrical passage being aligned with said axis substantially parallel to the arm, in which said first face has a series of holes therein extending parallel to the axis of the cylindrical passage and equidistant therefrom, and in which the second part carrying the sternum-engaging retractor blade means comprises a cylinder extending into said cylindrical passage from said first face, said cylinder closely fitting said cylindrical passage and being rotatable therein, a collar on said second part, pin means extending from said collar into at least one of said holes and thereby locking the second part against rotation relative to the first part, said pin means being capable of entering different holes in said series of holes to lock the second part in any selected one of a plurality of rotational relationships with said first part, a threaded hole in the end of said cylinder open toward the second face of said body, and screw means threaded into said threaded hole, said screw means having a head for manual turning thereof, and a shoulder for engaging the second face of the body, whereby, by tightening the screw means, the pin means can be securely held in selected holes to lock the first and second parts in selected rotational relationships.

3. A sternal retractor for use in internal mammary artery dissection comprising:

a rack bar;

a pair of spreader arms connected to the rack bar and extending substantially perpendicular to the rack bar and substantially parallel to each other, one of the spreader arms being movable along the rack bar whereby the spacing between the arms can be adjusted;

means connected to the rack bar and to the spreader arm movable thereon for applying a force causing the spreader arms to separate from each other while being maintained in substantially parallel relationship to each other; and means for engaging and spreading split sternal halves comprising sternum-engaging retractor blade means attached to each of said spreader arms;

at least one of said spreader arms comprising a first part connected to the rack bar and a second part carrying the sternum-engaging retractor blade means on said one of said spreader arms, means joining and locking said first and second parts against relative rotation about an axis of relative rotation substantially parallel to the arm, said joining and locking means being disengagable to allow adjustment of the rotational relationship of the first and second parts about said axis;

in which each of said spreader arms comprises a first part connected to the rack bar and a second part carrying sternum-engaging blade means, means joining and locking the said first and second parts against relative rotation about an axis of relative rotation substantially parallel to the arm, said joining and locking means being disengagable to allow adjustment of the rotational relationship of said first and second parts about said axis, and having slide means on each of the second parts of the spreader arms, the slide means being movable along said second parts, means for preventing rotation of said slide means on said second parts, and releasable clamping means for clamping said slide means against sliding movement on their respective spreader arms, said sternum-engaging blade means being carried by said slide means whereby the distances from the blade means to the rack bar can be adjusted.

4. A sternal retractor according to claim 3 in which at least one of said slide means has a slot in an exterior face thereof extending parallel to the second part of the spreader arm on which said slide means is movable, said slot being open to at least one end of said one of said slide means and having an undercut portion, a mounting post for an auxiliary retractor having a threaded opening in one end thereof said end bearing against the slotted exterior face of said slide means, and a screw having a shank threaded into said threaded opening in the mounting post and extending into said slot, and a head located in the undercut portion of the slot.

* * * * *